US006238362B1

(12) United States Patent
Bracht

(10) Patent No.: US 6,238,362 B1
(45) Date of Patent: May 29, 2001

(54) CONTOUR OF A TRANSDERMAL THERAPEUTIC SYSTEM

(75) Inventor: Stefan Bracht, Ochtendung (DE)

(73) Assignee: LTS Lohmann Therapie-Systeme AG (DE)

( * ) Notice: Subject to any disclaimer, the term of this patent is extended or adjusted under 35 U.S.C. 154(b) by 0 days.

(21) Appl. No.: 09/308,975

(22) PCT Filed: Nov. 20, 1997

(86) PCT No.: PCT/EP97/06485

§ 371 Date: Jul. 8, 1999

§ 102(e) Date: Jul. 8, 1999

(87) PCT Pub. No.: WO98/26740

PCT Pub. Date: Jun. 25, 1998

(30) Foreign Application Priority Data

Dec. 16, 1996 (DE) ................................... 196 52 269

(51) Int. Cl.$^7$ ................................................ A61F 13/00
(52) U.S. Cl. ................................ 602/41; 602/42; 424/449
(58) Field of Search ............................ 602/41–59, 900, 602/903; 128/888, 889, 890, 891; D24/189; 424/443, 444, 445, 446, 447, 448, 449

(56) References Cited

U.S. PATENT DOCUMENTS 4,666,441   5/1987   Andriola et al. .
4,709,695   12/1987  Kohn et al. .
4,719,909   1/1988   Micchia et al. .

*Primary Examiner*—Kim M. Lewis
(74) *Attorney, Agent, or Firm*—D. Peter Hochberg; Katherine R. Vieyra; William H. Holt

(57) ABSTRACT

A transdermal therapeutic system (TTS) for the delivery of active compounds to or through the skin, having a layer adhering comparatively permanently to the skin, whose outer edges are defined by a contour, is characterized in that at least two sections which are concave relative to the surface are contained in the contour.

6 Claims, 6 Drawing Sheets

5 6 10 11 7 8 9

CONTOUR OF A TRANSDERMAL THERAPEUTIC SYSTEM

The invention relates to a transdermal therapeutic system (TTS) for the delivery of active compound to or through the skin, having a layer adhering comparatively permanently to the skin, whose outer edges are defined by a contour. Below, TTS is to be understood as meaning transdermal therapeutic systems adhering to the skin either over part of the surface or over the whole surface.

A technical problem in the development of TTSs is the guarantee of a contour-sealing combination with the skin when wearing for periods of 24 hours up to 7 days or more. Contour-sealing in this connection means that detachment of an outer edge of the TTS from the skin is largely avoided.

In order to guarantee an adhesive combination of a TTS with the skin for comparatively long periods, on the one hand an optimization of the adhesive layer on the skin side is necessary. Depending on the construction of the TTS, this layer can be active compound-containing and moreover can contain pharmaceutical auxiliaries which favour the dermal permeation of the active compound. In such cases, the adhesive behaviour of the layer is affected to a greater or lesser extent by the nature and amount of the active compounds and auxiliaries contained. On the other hand, additional effects on the wearing behaviour originate from the size of the TTS and from the administration site on the human body. The mechanical forces acting on the TTS (e.g. stretching, compression and shear forces), which can lead to an at least partial detachment from the skin, substantially result from these two parameters.

The establishment of optimum adhesive properties is an object concerning the formulation of the adhesive layer, which optionally contains active compound, and depends strongly on the internal and external construction of the TTS. The variabilities associated therewith make the generalization of successful formulations largely impossible. For each new TTS, as a rule a more or less laborious optimization of the adhesive properties is therefore necessary.

However, a contour-sealing long-term application of a TTS to the skin is affected to a considerable extent by the outer shapes of a TTS in the sense of the course of its contour, which depending on its design can mechanically prevent the detachment of the outer edges of a TTS when it is worn on the skin and can thus advantageously delay it.

The fixing of the outer contour of TTSs conforms, according to the prior art, to the following criteria:

1. The production of a TTS in its final form is customarily carried out by separation from a thin-layer, strip-like material. It can be, for example, a question of punching at regular intervals with a flat punching tool or continuous cutting with a cylindrical cutting tool. In this case, the production of a contour of a TTS preferably aims at as low an amount as possible of waste during punching or cutting. This applies in particular in the case of active compound-containing waste. Since the starting material, as a rule, has a multilayer, complex construction, reutilization of the waste is often impossible or unprofitable.

The waste reduction thus has a large role among the criteria for the production of a contour in TTS production.

2. Under the aspect of decreased detachment behaviour of a TTS which is stuck to the skin, acute angles of <90° are avoided in the contour. Such tips are particularly exposed points for detachment from the skin and are avoided as a result of this. Right-angled corners are rounded, which has proved in practice to be a suitable means for reducing corner detachment and finds general application.

3. The outer shape of a TTS must produce no aversion to application and wearing on the skin for patients. It must therefore favour simple application and easy removal. Simple geometric contours have proved suitable. In the prior art, this has led to TTS contours which are defined by the shapes of the circle, the ellipse, the rectangle, the square or other polygons. FIG. 1 shows an exemplary selection of the customary shapes.

The document U.S. Pat. No. 4,666,441 discloses a TTS whose contour contains concave sections. What is referred to here is the product "Estracombi"® from Ciba. The shape of this system, which outside technical terminology is also called a "glasses patch" is, however, not connected according to the invention with an improvement in the contour-sealing combination with the skin. On the contrary, the construction serves for a chambering of the liquid reservoir contained. The proportion of the concave contour sections in the total length of the outer TTS contour is moreover less than 10 per cent.

Outside the TTS group, other skin-adhesive systems are known whose contours in some cases include concave sections. In contrast to TTSs, these are essentially more flexible plasters or plaster-like elements such as:

wound plasters for application on the eye (e.g. U.S. Pat. No. 4,709,695).

UV protective plasters for application in the area underneath the eye (e.g. U.S. Pat. No. 4,719,909).

Skin-adhesive hydrogels for cosmetically affecting the skin condition in the area under the eye (e.g. DE 44 46 380).

Plasters to prevent the growing-in of the toenail on the big toe (e.g. DE 38 23 889).

Plasters for spreading the nasal wings and thereby improving breathing through the nose (e.g. Breath Wright™ in the USA).

It is common to all these relatively flexible skin-adhesive systems that in them the concave contour course is prespecified by individual anatomical conditions at the application site. Shaping is in this way tailored to the human anatomy.

Figure 1:
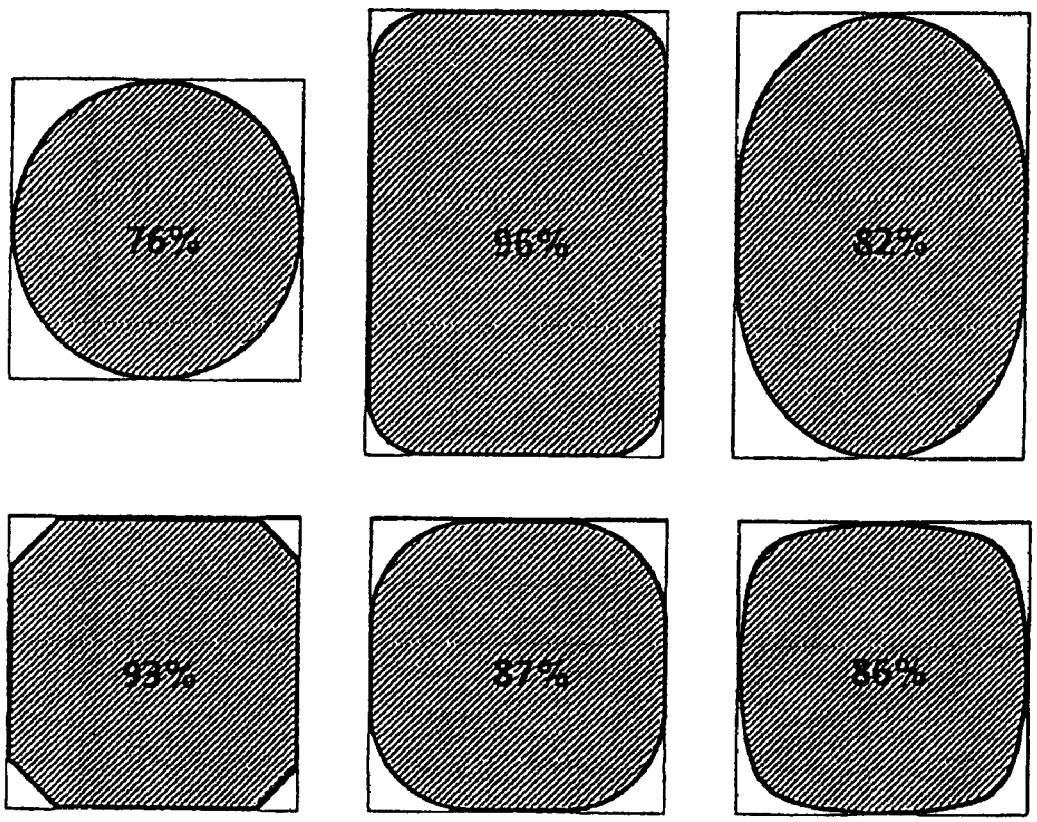
FIG. 1 shows a selection of customary TTS shapes.

The invention is based on the object of realizing contours in a TTS which are designed such that they afford a significant contribution to the improvement and prolongation of a contour-sealing combination of the TTS with the skin.

The object is achieved in a transdermal therapeutic system for the delivery of active compounds to or through the skin comprising a layer adhering comparatively permanently to the skin whose outer edges are defined by a contour, with said transdermal therapeutic system having at least two concave sections present in its contour.

According to a preferred embodiment of the invention, at least 30% of the total length of the contour is allocated to the concave contour sections in total.

Surprisingly, in spite of approximately 2 decades of TTS development and a large number of products on the world market, this route to a solution has previously not been followed. To date, the development of TTSs includes, as major focal points, the optimization of the active compound delivery and the adhesive properties of the skin-adhesive formulation. Little attention was previously paid here to the effects of the outer shape, in particular on the long-term wearing behaviour.

The mechanical forces acting between areas of skin and a self-adhesive TTS are mainly shear forces. The skin lying below the TTS is extended or compressed to a greater or lesser extent by stretching or bending of the nearest joints in each case. Irregular contractions and relaxations of the underlying skeletal musculature, which is present in almost all application areas of the human body, likewise lead to extension or compression of such an area of skin.

Besides the shear forces which are transmitted by the adhered skin, further shear and peeling forces act on a TTS if clothing is worn over it. The forces are highly dependent on the composition of the outer layer of the TTS and the covering textiles. These peeling forces have a great effect on the detachment of the TTS from the skin, in particular if a small part of the edge of the TTS has already come away from the skin. These raised sections, which as a rule are sticky, are easily carried along with textiles, and thus initiate an accelerated peeling-off of the entire TTS.

An important special case of the interaction of the TTS with textiles occurs when the patient is sleeping. At almost each of the abovementioned customary application sites, there is the possibility that the sleeping person lies on the TTS itself. In the case of body movement, this readily leads to a transmission of considerable shear or peeling forces to the TTS over a wide area.

The action of shear forces on the adhesion of a TTS is presented in simplified form in terms of a model below. In the area of a TTS applied to the skin, hypothetical adhesion or sticking points are shown. These positions, subsequently described as holding points, are the equivalent of actual molecular interactions between the skin surface and TTS. For reasons of clarity, they are arranged regularly distributed over a surface (FIGS. 2a and 2b), while the real distribution is assumed to be stochastic.

For the holding points, it is furthermore assumed that each of them interacts with its immediately adjacent holding points in a direct mechanical interaction. A TTS according to the prior art has a significantly lower elasticity than the human skin. In many cases, a TTS can be considered as nearly-inelastic in comparison with the skin. In the model, therefore, the effort of the skin surface to carry out a relative motion against the comparatively rigid layer of the adhered TTS is shown as an effect of shearing. This relative motion does not have to relate to the entire adhered surface, but can be restricted to parts thereof in the case of large TTSs. For the shear force model, the premise, which is close to reality, of a skin detaching from the TTS is valid in comparison with an obvious but wrong idea of a TTS detaching from the skin.

Figure 2A:
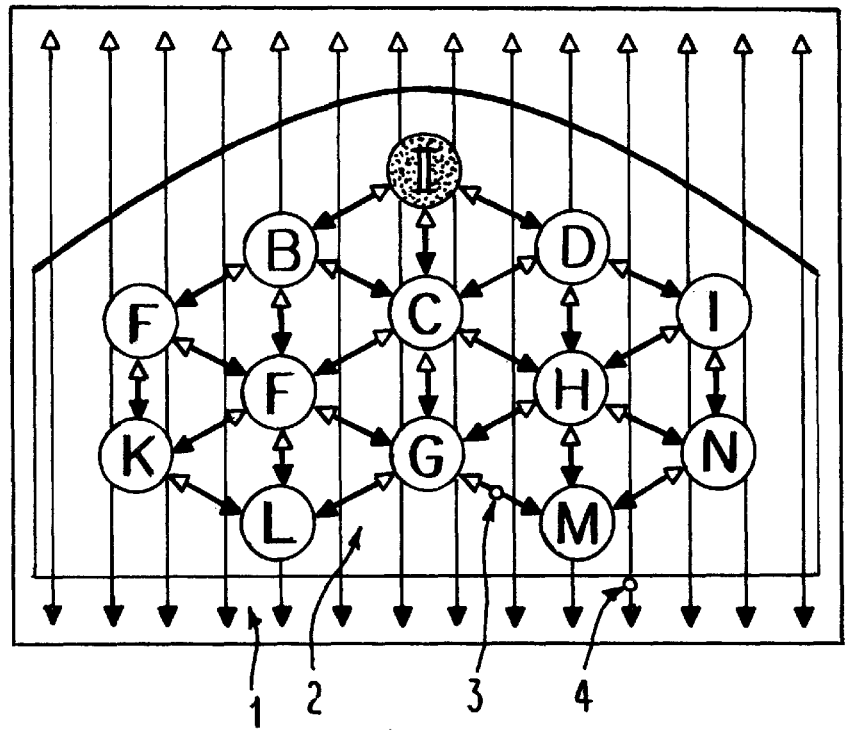
FIGS. 2a and 2b shows the action of shear forces on the adhesion of a TTS when the TTS is applied to the skin.
Figure 2B:
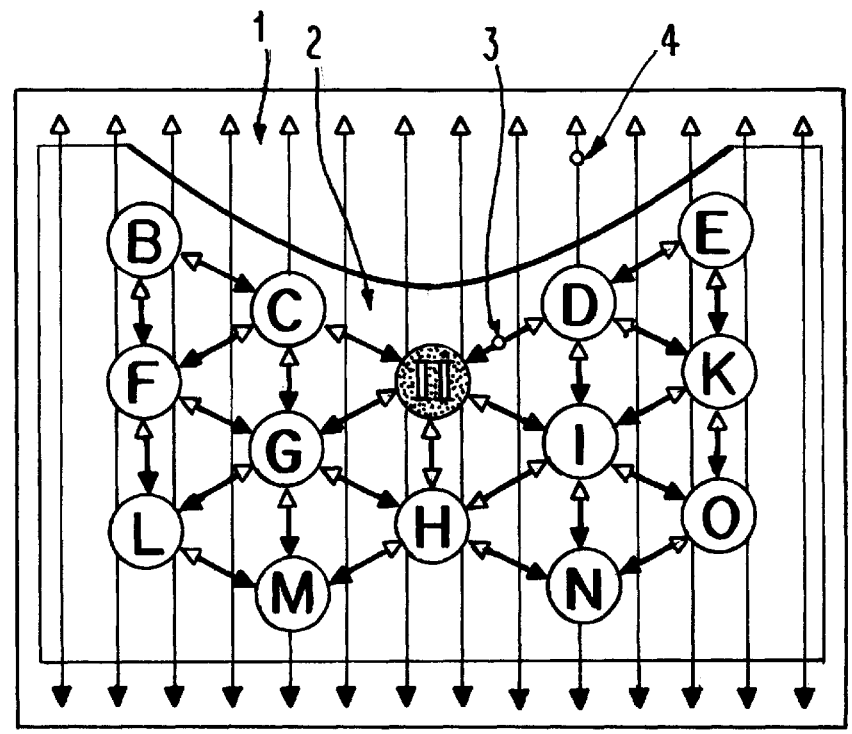

The model is used for the consideration of the processes on a convex and a concave contour section (FIGS. 2a and 2b). The projection of the TTS surface produced in the convex contour is described as a cliff, the foremost holding point as a cliff point (I) (FIG. 2a). In the concave contour, however, appears a bay and the holding point the furthest behind in this bay is described as a bay point (II) (FIG. 2b).

The acting shear forces are shown by (4) vectors (with open/closed heads) representing shear forces, which lie in the planes of the adhered skin 1. In the simplification, these are directed either away from the indicated (21) TTS surface 3 (open arrow end) or else towards it (closed arrow heads). Under the action of these shear forces, mechanical interactions of the holding points with one another occur. These forces are likewise symbolized by (3) vectors representing interactions between holding points, whose orientation depends on those of the acting shear forces and which therefore have the corresponding arrow head representation in the drawing. While the cliff point I in FIG. 2a interacts with only three adjacent holding points B, C, D, the bay point II in FIG. 2b interacts with five of its neighbours.

However, the number of interaction possibilities for other holding points B, D lying on the outer edge of the surface in FIG. 2a and C, D in FIG. 2b is identical both in a bay and on a cliff.

The different conditions at cliff point I and bay point II lead to a preferred tearing, under identical shearing, of the skin 1 from the cliff point I compared with the bay point II. This is based on the fact that the holding of the skin 1 on a cliff point I is assisted by fewer adjacent holding points than on a bay point II.

Figure 3A:
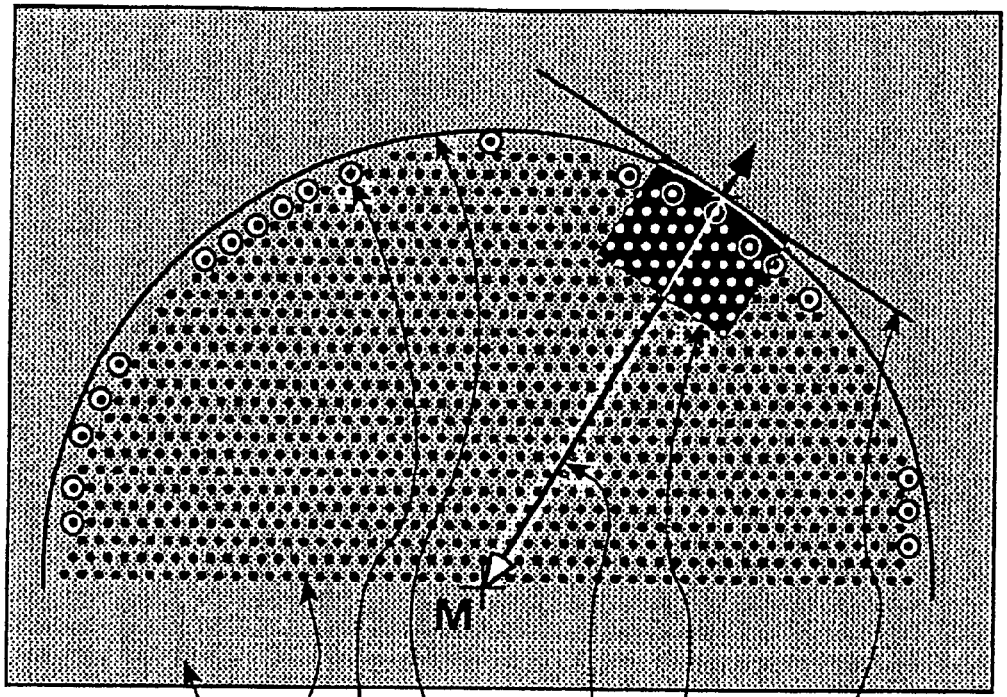
FIG. 3 show acting shear forces which lie in the planes adhered to the skin.
Figure 3B:
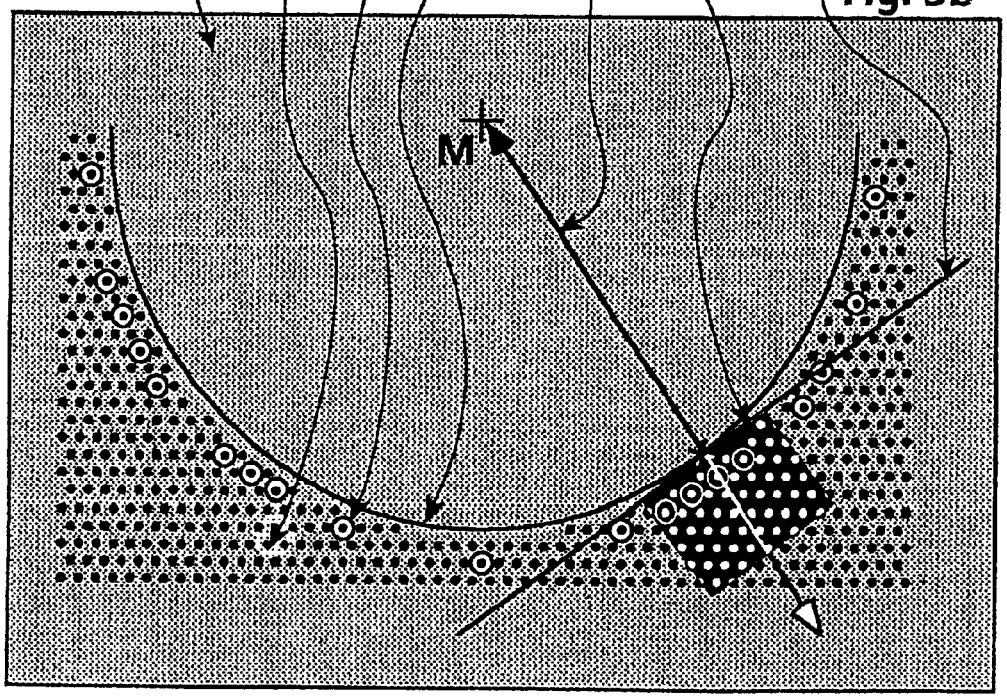

If in a concave, bay-like contour section of a TTS, only a single bay point II, or in the opposite case of a cliff-like convex section, only a single cliff point exists, the advantage resulting therefrom would be negligible. Actually, however, a very large, finite number of such points exists in a curved contour section, depending on the direction of the vector field of the shear force in the adhered skin surface 1. In FIGS. 3a and 3b, this is shown on a semicircular cliff or a semicircular bay. Depending on the orientation of the shear force 3, according to FIGS. 2a, 2b cliff or bay points result on the outer edge of the TTS 2. These (10) particular holding points are encircled in FIGS. 3a and 3b. Their position results in the simplified presentation near the intersection point of the TTS contour 11 with that shear force vector 7 which is located through the centre M of the arc of the circle. With the aid of the tangent 9 to the arc of the circle 11 through this intersection, a large number of cutouts can be identified in analogy to those shown in FIGS. 2a and 2b.

From the large number of possible bay and cliff points within a curved TTS contour, a clear advantage of concave contours in comparison with convex contours can be recognized.

A further advantage of the contour according to the invention relates to the effect of shear forces on the detachment of a TTS from the skin 1.

Figure 4:
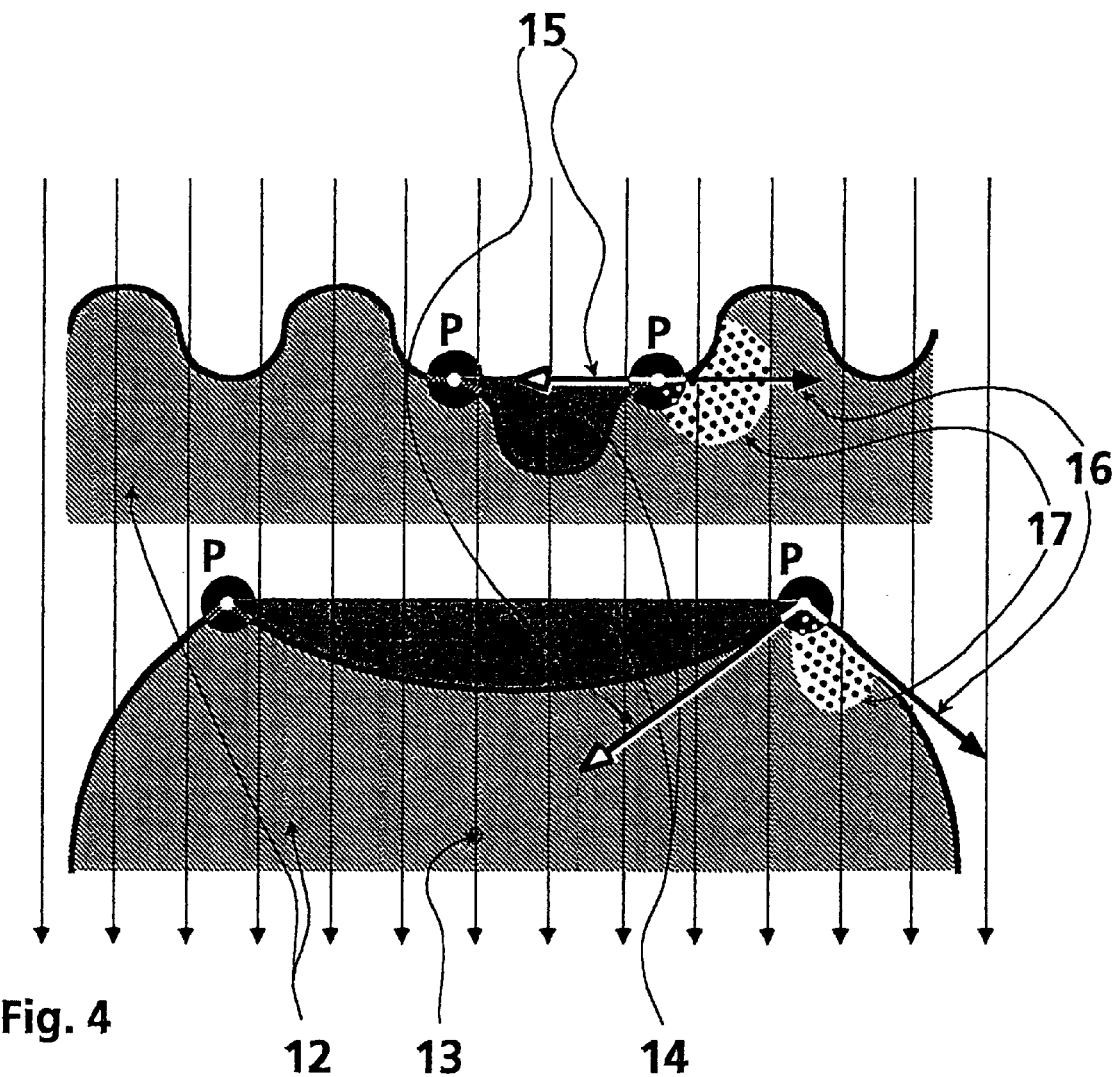
FIG. 4 shows the detachment process for a wavy and for a simple, curved convex contour.

As long as a contour-sealing combination of the TTS with the skin exists, peeling forces have few possibilities of attack. If, however, a detached site is present, the detachment, in particular in frictional contact with textiles, can proceed rapidly by means of peeling. The stickiness of the detached layer is so greatly decreased by the adhering skin surface constituents and by entering textile fibres that a fresh, permanent adhesion of the detached part to the skin is virtually impossible. Partial detachment of the TTS during wearing is therefore as a rule irreversible, and so preventive measures have particular importance. In FIG. 4, the detachment process for a wavy and for a simple, curved convex contour is shown diagrammatically.

Sections of a TTS surface 12 adhering to the skin are shown, from which a part 14 has detached in each case. The detached parts 14 are shown in simplified form with the top end bent back at an angle of 180° towards the inside of the TTS. The peeling forces having a detaching action correspond to a field of (13) TTS—inwardly directed vectors.

This approximates, for example, to the action of a layer of textiles, as a rule laying flat on the skin, which adheres to the detached TTS surface parts 14 and has a considerable detaching action at a peeling angle of 180°. Those points P on which the already detached TTS outer edge meets with the TTS outer edge still adhering to the skin are of particular importance for the theoretical consideration. In the case of a wavy contour, the detachment initially proceeds largely as in the case of a simple, convex cut as far as the state shown in FIG. 4. At the point P, the detached contour now has the same spatial orientation in the plane as the still adhering contour. This is shown by corresponding orientation vectors 15, 16. Within the meaning of a mathematical curve discussion, the contour here has the gradient zero.

At a 180° peeling angle to the resulting tongue, attacking tractive forces now act on a wavy contour via the point P on an area of holding points of the TTS which is shown in section in FIGS. 3a, 3b. It is evident that the next indentation of the TTS still adhering to the skin contains considerable holding points which counteract further detachment. In the case of a simple convex contour, this condition, however, does not occur at any time. At the point P, the orientations of the detached and of the still adhering outer edge never lie on a common straight line. At any time, the point P is a cliff point, and so a further detachment is still favoured according to the above details.

A further advantage of a wavy contour lies in the better fitting of the TTS to curved application surfaces and relates in particular to large-area TTSs. Curved application surfaces are understood here to mean surfaces which are curved in more than one direction in space. A surface which is only curved in one direction in space (for example a cylindrical surface) can be covered in a fold-free manner with a TTS which has been punched out of a flat sheet material. For a surface which is curved in several directions in space (example: surface of a hemisphere), however, this does not apply. While the surface area of a hemisphere increases with the 3rd power of its radius, the area of a circular TTS increases only with the 2nd power of the radius. The impossibility of the fold-free covering of a hemispherical surface with a TTS produced as a flat surface results from this. This problem can be transferred to the adhesion of certain areas of skin of the body. Thus, for example, parts of the shoulder, chest, abdomen and seat can be considered approximately as surfaces of hemispheres, and the application of large-area TTSs here readily leads to fold formation. As a result of fold formation, however, the contact surface to the skin is reduced and thus the active compound delivery per time from the TTS is undesirably decreased. Moreover, the detachment of the TTS from the skin by adhesive and sliding friction is accelerated on raised folds.

Figure 5:
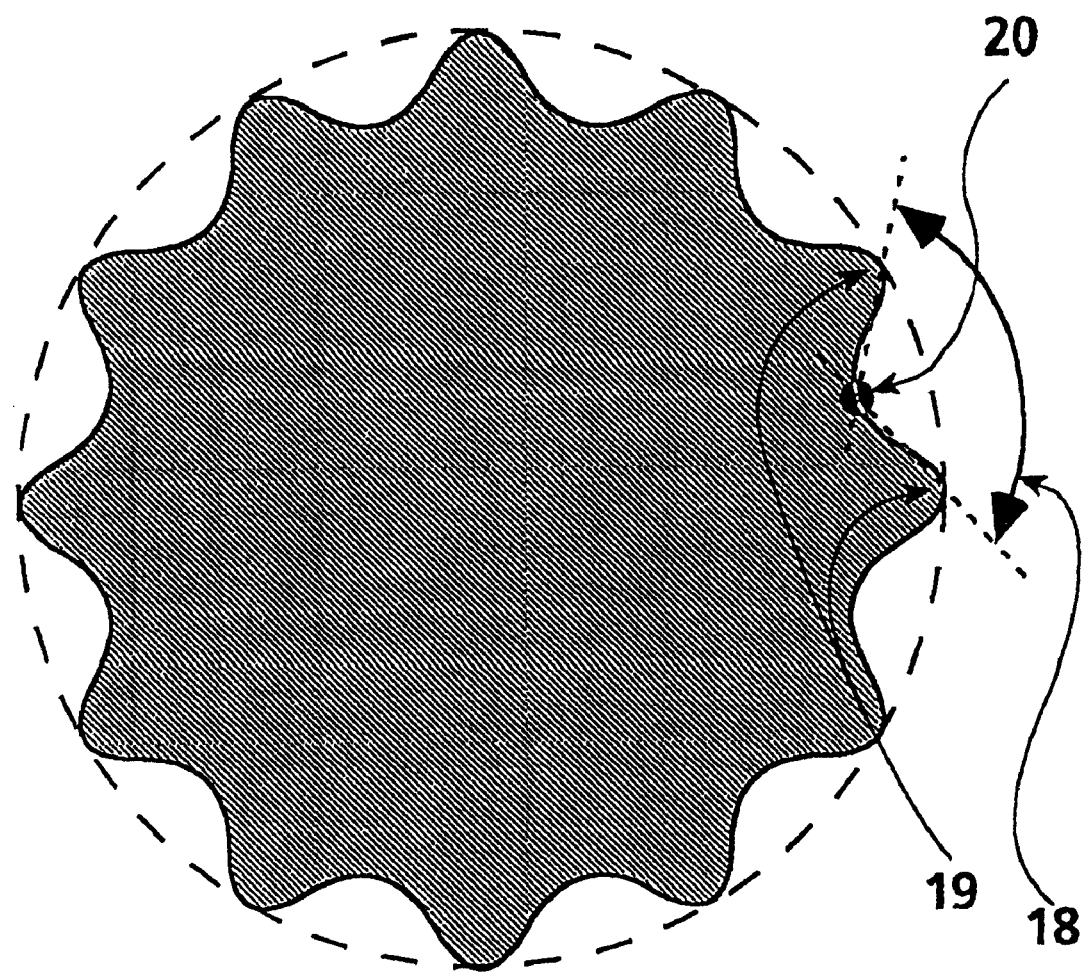
FIG. 5 shows the cliff-like extensions of the TTS surface.

In principle, the problem can be alleviated by the use of elastic or plastic materials in TTS production. Such materials would together be able to carry out the generation of a spherical surface, which, compared with the flat surface, is more than proportional to the radius, by elastic or plastic extension. Both the plastic and the elastic extension of a TTS, however, are accompanied by an increase in its original area with a simultaneous decrease in the thickness. This is undesirable, since both the increase in the delivery surface on the skin, and a decrease in the layer thickness of the TTS, uncontrollably affect the active compound delivery to the body. By means of a wavy contour, extensions and folds on the adhesion of a curved surface can admittedly not be avoided in principle, but can be decisively decreased. The cliff-like extensions of the TTS surface shown in exaggerated form in FIG. 5 are able to offset the effects mentioned, in particular in the edge region. As a result of the more than proportional growth of the curved area to be adhered, extensions caused can largely be compensated for by spreading 18 of two adjacent cliff-shaped sections 19. The plastic or elastic deformation of the TTS is in this way reduced to small areas on the intermediate bay points 20. In particular in the edge region, the contour-sealing combination of the TTS with the skin, which is important from the point of view of the long-term adhesion, is thus facilitated.

In summary, those TTSs which according to the invention contain concave sections in their contour have a number of advantages relating to the long-term contour-sealing combination with the skin. At the same time, they can usually be prepared without additional technical expenditure compared with the customary TTS preparation procedures and have a surface utilization which is only insignificantly lower than in the case of the usual TTS contours according to the prior art.

Figure 6:
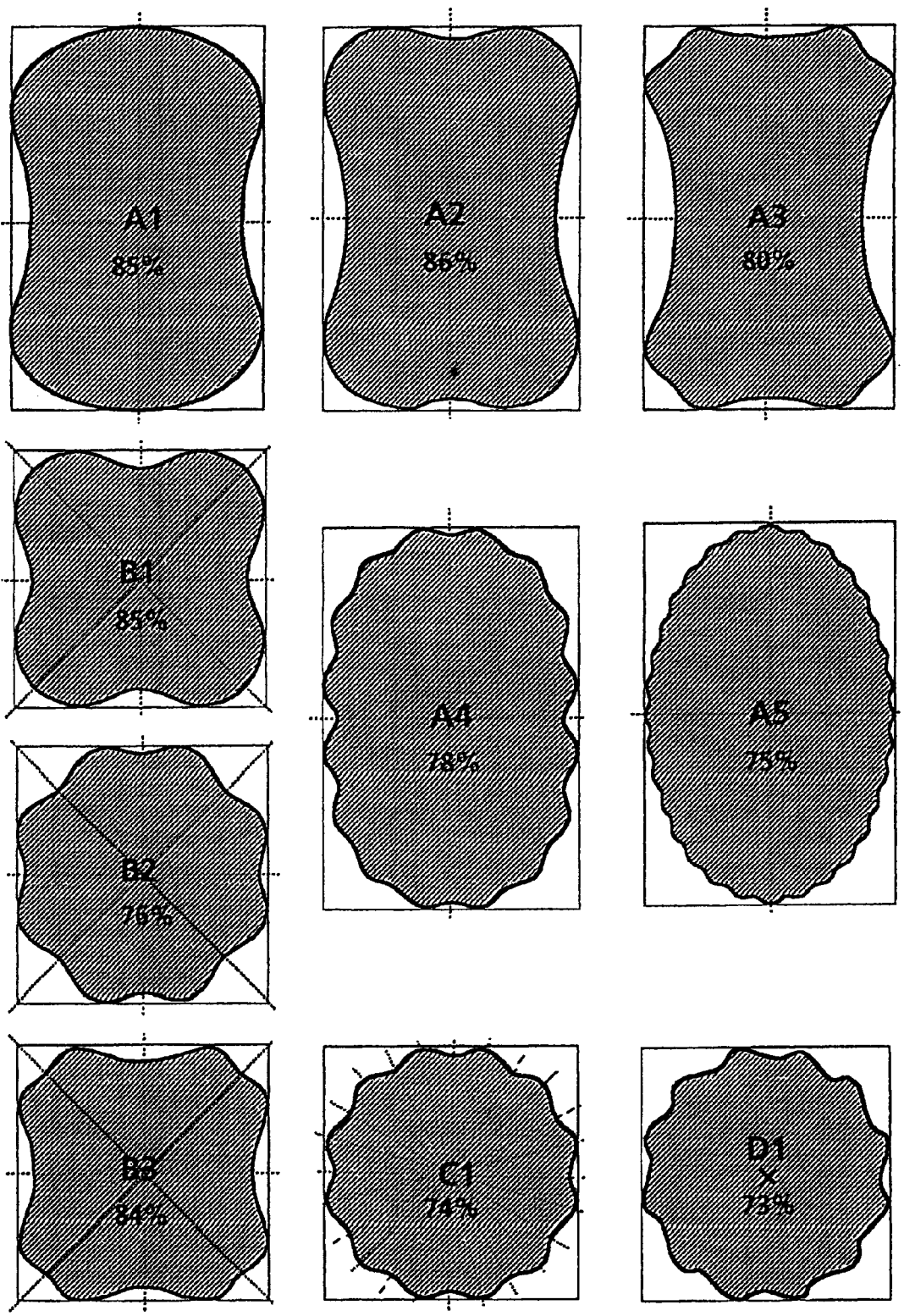
FIG. 6 shows the area utilization coefficient for convex contour TTS shapes indicated in per cent for each type of design.

FIG. 6 gives an exemplary, but not complete, overview of the novel contours according to the invention and their preferred shape.

Systems of type A are characterized by the presence of 2 planes of symmetry in the contour. Preferred variants of this type are shown having 2 ($A^1$), 4 ($A^2$) and 8 ($A^3$) concave sections in the contour. In the case of an even greater number of concave sections, for example, contours result having a coarse ($A^4$) or fine ($A^5$) wavy course. The systems of type A have an even number of n=2 to n=50 concave sections in the contour.

Systems of type B are characterized by the presence of 4 planes of symmetry. The preferred variants have 4 ($B^1$) or 8 ($B^2$, $B^3$) concave sections in the contour. A greater number of concave sections is even possible, from which contours in analogy to those having 2 planes of symmetry of the type $A^4$ and $A^5$ then result. The systems of type B have an even number of n=4 to n=50 concave sections in the contour. Systems of type C are of radially symmetrical construction. Radially symmetrical is to be understood as meaning that all planes of symmetry start at a single common point within the surface of the TTS. The number of concave sections in the contour is n=5 to n=50 and is even-numbered or preferably odd-numbered.

Systems of type D have a point symmetry-running contour. The point of symmetry lies within the surface of the TTS. The number of concave sections is n=3 to n=50 and the number n assumes even-numbered or odd-numbered values.

In FIG. 6, the area utilization coefficient is indicated in per cent for each type of design ($A^1$, $A^2$, $A^3$, $A^4$, $A^5$, $B^1$, $B^2$, $B^3$, $C^1$, $D^1$). The area utilization coefficient is to be understood as meaning the ratio of the area of the TTS to the area of the smallest rectangle circumscribing its. contour. Higher values mean a higher yield in the production of individual shapes from a flat precursor and are therefore more favourable than low values.

What is claimed is:

1. Transdermal therapeutic system for the delivery of active compounds to or through the skin comprising a layer adhering comparatively permanently to the skin, whose outer edges are defined by a contour containing at least two sections which are concave relative to the surface of the layer.

2. The transdermal therapeutic system of claim 1 wherein at least 30% of the total length of the contour is allocated to the concave contour sections in total.

3. The transdermal therapeutic system of claim 1 wherein the contour has two planes of symmetry, and the number of concave sections is between 2 to 50 and is even-numbered.

4. The transdermal therapeutic system of claim 1 wherein the contour has four planes of symmetry, and the number of concave sections is between 4 and 50 and is even-numbered.

5. The transdermal therapeutic system of claim 1 wherein the contour runs radially symmetrically and contains between 3 to 50 concave sections.

6. The transdermal therapeutic system of claim 1 wherein the contour runs point-symmetrically to a point lying in the surface of the transdermal delivery system and contains from between 3 to 50 concave sections.

* * * * *